US009974823B2

(12) United States Patent
Faraggi

(10) Patent No.: US 9,974,823 B2
(45) Date of Patent: May 22, 2018

(54) COMPOSITION COMPRISING NATURAL EXTRACTS

(71) Applicant: INNO-BEV LTD., Tel Aviv (IL)

(72) Inventor: Eli Faraggi, Tel Aviv (IL)

(73) Assignee: INNO-BEV LTD., Tel Aviv (IL)

( * ) Notice: Subject to any disclaimer, the term of this patent is extended or adjusted under 35 U.S.C. 154(b) by 825 days.

(21) Appl. No.: 13/917,129

(22) Filed: Jun. 13, 2013

(65) Prior Publication Data
US 2013/0337093 A1 Dec. 19, 2013

Related U.S. Application Data

(60) Provisional application No. 61/659,155, filed on Jun. 13, 2012.

(51) Int. Cl.
A61K 36/77 (2006.01)
A61K 36/185 (2006.01)
A61K 36/16 (2006.01)

(52) U.S. Cl.
CPC .............. A61K 36/77 (2013.01); A61K 36/16 (2013.01); A61K 36/185 (2013.01)

(58) Field of Classification Search
None
See application file for complete search history.

(56) References Cited

U.S. PATENT DOCUMENTS

| 6,413,558 | B1* | 7/2002 | Weber | A23L 2/38 424/729 |
| 2005/0202104 | A1* | 9/2005 | Gianesello | A23L 1/3002 424/725 |
| 2006/0134300 | A1 | 6/2006 | Newman | |
| 2006/0147600 | A1 | 7/2006 | Gonzales et al. | |
| 2008/0219964 | A1* | 9/2008 | Keefe | A23L 1/30 424/94.2 |

FOREIGN PATENT DOCUMENTS

| DE | 10 2004 017 512 A1 | 10/2005 |
| EP | 1 671 550 A1 | 6/2006 |
| WO | 03/101225 A1 | 12/2003 |
| WO | 2006/065255 A1 | 6/2006 |

OTHER PUBLICATIONS

Marasco (Drug Exptl. Clin. Res. (1996) vol. 22, No. 3, pp. 323-329).*
Sass, "Functional Ingredients with Measurable Health Benefits", Fruit Processing, vol. 18, No. 1, pp. 14-16, (Jan./Feb. 2008).
Schimpl et al., "Guarana: Revisiting a highly caffeinated plant from the Amazon", Journal of Ethnopharmacology, vol. 150, No. 1, pp. 14-31, (2013).
Schinz, "Sweeteners: Fruit sweeteners: In vogue", Int Food Info Service, vol. 66, No. 4, pp. 174-175, (1999). In German with English Translation attached separately.
Smith et al., "Guarana's Journey from Regional Tonic to Aphrodisiac and Global Energy Drink", Advance Access Publication (2007), eCAM, vol. 7, No. 3, pp. 279-282, 2010.
Tanaka et al., "Effects of the Flavonoid Fraction from Ginkgo biloba Extract on the Postprandial Blood Glucose Elevation in Rats", Yakugaku Zasshi, vol. 124, No. 9, pp. 605-611, (2004). English Abstract on p. 605.
Haskell, et al., "A double-blind, placebo-controlled, multi-dose evaluation of the acute behavioural effects of guaraná in humans", Journal of Psychopharmacology, vol. 21, No. 1, pp. 65-70, (2007).
Kennedy, et al., "Improved cognitive performance in human volunteers following administration of guarana (*Paullinia cupana*) extract: comparison and interaction with Panax ginseng", Pharmacology, Biochemistry and Behavior, vol. 79, pp. 401-411, (2004).

* cited by examiner

Primary Examiner — Susan Hoffman
(74) Attorney, Agent, or Firm — Vorys, Sater, Seymour & Pease LLP

(57) ABSTRACT

The invention relates to a method for providing an awaking effect and specifically affecting post lunch dip in a subject comprising providing a subject with a composition comprising an isolate of guarana plant, and at least one of (i) isolate of *ginkgo biloba* plant or functional analog thereof and (ii) fruit sugars, wherein the composition does not affect the subject's heart activity. The invention further provides a method for affecting post lunch dip in a subject, comprising administering to the subject a daily dose of a composition comprising (i) an isolate of guarana plant, (ii) an isolate of *ginkgo biloba* plant or functional analog thereof and (iii) fruit sugars for a period of at least 7 days.

16 Claims, 8 Drawing Sheets

COMPOSITION COMPRISING NATURAL EXTRACTS

TECHNOLOGICAL FIELD

This invention relates to compositions comprising plants extracts that improve the well being of a subject.

BACKGROUND

Plants formulations are widely used to provide health benefits. For example plants such as guarana, *ginkgo biloba*, *ginseng* [sp] and others were previously reported to improve health conditions either when used alone or in combinations with additional ingredients.

For example, guarana seeds were described to have stimulant effects which are generally attributed to the presence of caffeine comprising 2.5%-5% of the extract's dry weight [Haskell C F et al., *J. Psychopharmacology*, 21, 65-70; 2007]. In this publication, Guarana was described to exhibit psychoactive properties being attributed to high content of additional possible psychoactive components including saponins and tannins. Further, this publication shows the effect of guarana on mood with dose dependent increase in alertness and contentedness. As described, two low concentrations (37.5 mg and 75 mg extracts) allegedly provided more beneficial cognitive effects as compared to two higher concentrations (150 mg and 300 mg extracts).

Further, it was described that administration of 75 mg of dried ethanolic extract of guarana (approx 12% caffeine) to non-fatigue individuals led to improvement in secondary memory and speed of attention. It was hypothesized that given the low caffeine content (9 mg) of this dose of guarana extract, the effects were unlikely to be attributable to its caffeine content [Kennedy D O et al., *Pharamcol, Biochem Behav,* 79: 401-411; 2004].

In some other publications, such as International Application Publication Nos. WO06/065255 and WO03/101225 compositions are describes as comprising a plant extract (for example guarana, *ginkgo* and *ginseng*) mixed with caffeine and/or taurine and sugars.

SUMMARY OF DESCRIPTION

In its broadest aspect, the present disclosure provides a composition comprising as active components (i) an isolate of guarana plant at least one of (ii) an isolate of *ginkgo biloba* plant or functional analog thereof and (iii) fruit sugars. In this context, there is also provided a method comprising administering the composition to a subject.

In some aspects, the present disclosure provides a composition comprising an isolate of Guarana plant and at least one of (i) isolate of *ginkgo biloba* plant or functional analogue thereof and (ii) fruit sugars, the composition being for use in providing an awaking effect on a subject without exhibiting a detected effect on the subject's heart activity.

In some embodiments, the composition comprising as active components (i) an isolate of Guarana plant, (ii) an isolate of *ginkgo biloba* plant or functional analogue thereof and (iii) fruit sugars.

In some embodiments, in a 100 ml composition the following amounts of are included: (i) between about 30 mg guarana isolate to about 70 mg guarana isolate; (ii) between about 30 mg *ginkgo biloba* isolate to about 70 mg *ginkgo biloba* isolate; and (iii) between about 4 ml to about 15 ml fruit sugars. In some other embodiments, the composition also comprise elderberry. In yet some other embodiments, in 100 ml final composition the elderberry is present in an amount of between about 40 mg to about 60 mg.

Without being bound by theory, it is believed that the guarana and *ginkgo biloba* from plants, each contain between 20% to 30%, at times, between 24% to 29% and further at times, about 24% of active ingredients. As such, in some embodiments, in a 100 ml composition the following amounts of active components are included: (i) between about 6 mg guaranine to about 20 mg guaranine (at times between 7 to 17 mg); (ii) between about 6 mg to about 20 mg flavonoid glycosides (at times between 7 to 17 mg); and (iii) between about 4 ml to about 15 ml fruit sugars.

In some other aspects, the present disclosure provides a composition comprising (i) an isolate of guarana plant, (ii) an isolate of *ginkgo biloba* plant or functional analogue thereof and (iii) fruit sugars for use in ameliorating, inhibiting or reducing post lunch dip.

In some embodiments, the composition exhibits a medically negligible or no detected effect on the subject's heart activity following administration thereof to the subject. In some other embodiments, the subject's heart activity is determined by one or more parameters indicative of a subject's heart activity, said one or more parameters being selected from the group consisting of heart rate and blood pressure.

In some further aspects, the present disclosure provides a composition comprising (i) an isolate of guarana plant, (ii) an isolate of *ginkgo biloba* plant or functional analogue thereof and (iii) fruit sugars for use in ameliorating, inhibiting or reducing post lunch dip, wherein the composition is for use as a daily dose during a period of at least 7 days.

The composition is particularly suitable for oral consumption, e.g. in the form of a drink or in a form suitable for forming a drink (e.g. dissolvable or dispersible tablet, gel or capsule) and chewing gum and gummy bears.

The composition may be provided at any time either during or before post lunch dip is developed. Alternatively, the composition may be administered before noon or within a time window of up to an hour before post lunch is developed in a subject in need thereof.

The present disclosure also provides in some other aspects a method for providing an awaking effect on a subject, the method comprises providing a subject with a composition comprising an isolate of guarana plant, and at least one of (i) an isolate of *ginkgo biloba* plant or functional analogue thereof and (ii) fruit sugars, wherein the composition does not affect the subject's heart activity.

In some embodiments, there is provided a method for providing an effect selected from the group consisting of ameliorating, reducing and inhibiting development of post lunch dip.

In some further aspects, the present disclosure provides a method for affecting post lunch dip in a subject, comprising administering to the subject a composition comprising (i) an isolate of guarana plant, (ii) an isolate of *ginkgo biloba* plant or functional analogue thereof and (iii) fruit sugars for providing an effect on said subject selected from the group consisting of ameliorating, inhibiting and reducing post lunch dip.

In yet some other aspects, the present disclosure provides a method for affecting post lunch dip in a subject comprising administering to the subject a daily dose of composition comprising (i) an isolate of guarana plant, (ii) an isolate of *ginkgo biloba* plant or functional analogue thereof and (iii) fruit sugars for a period of at least 7 days, wherein said administration provides an effect on said subject selected from the group consisting of ameliorating, inhibiting and reducing post lunch dip.

In some embodiments, the composition is administered in an amount that provides a medically negligible or no detected effect on the subject's heart activity. In some other embodiments, the method comprises determining the subject's heart activity by one or more parameters selected from the group consisting of heart rate and blood pressure.

In some aspects, there is also provided a composition and method as defined herein, for daily administration

BRIEF DESCRIPTION OF THE DRAWINGS

In order to understand the disclosure and to see how it may be carried out in practice, embodiments will now be described, by way of non-limiting example only, with reference to the accompanying drawings, in which.

DETAILED DESCRIPTION OF EMBODIMENTS

Figure 1A:
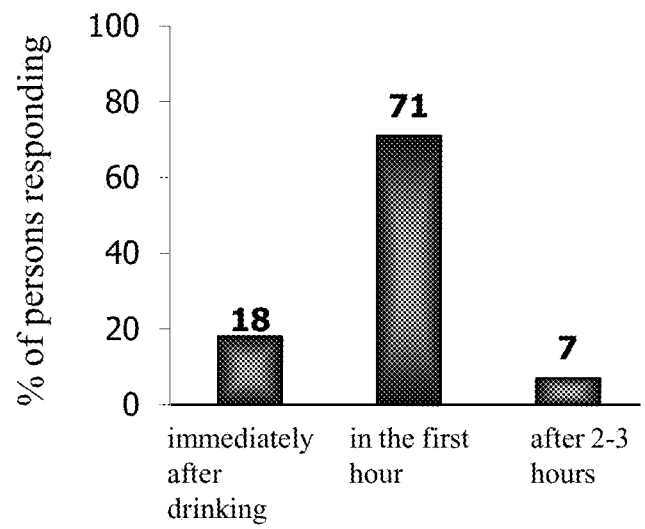
FIGS. 1A and 1B are bar graphs showing the effects of composition 1.

Energy drinks often include high amounts of (above 50 mg/100 ml) stimulates such as caffeine and/or taurine. Drinking coffee is also known to have waking effect. However, caffeine has a short half-life and potential side effects, such as increased pulse rate and blood pressure. In addition, regular coffee drinking, at times, results in tolerance and substantial reduction of the effect of caffeine. When referring to tolerance (physiological tolerance) it is to be understood as referring to a decrease in the response of a subject to the compositions disclosed herein, due to previous exposures to the composition.

The present disclosure provides alternative awakening compositions. In the broadest aspect, the present disclosure provides a composition for improving a subject's vigilance or performance without the negative side-effects of energy drinks currently on the market.

Specifically, the inventors developed compositions that lead to significantly improvement in cognitive capabilities and awakens parameters measured after lunch time, without increasing the subject's blood pressure and blood rate to an extent typically occurring after drinking coffee or energy drinks having high amounts of caffeine, taurine or the like. In addition, the inventors found that when the developed composition was used on a daily basis for a period of several days no tolerance to the composition's effect was observed.

Further, the inventors compared the effect following drinking of a composition disclosed herein to the effect of drinking caffeine and observed that the composition disclosed herein was at least as good as caffeine in its capability to improve awakens and metal capabilities. However, while caffeine consumption resulted in an increase in blood pressure and blood rate, the composition disclosed herein was advantageous as it was not associated with any similar increase in heart activity.

In addition, use of the composition disclosed herein, on a daily basis, for a period of several days, resulted in a gradual improvement of cognitive measures (e.g. accumulated effect). In other words, the inventors observed a gradual increase in the measured parameters over time of the study. Thus, in accordance with its first aspect the present disclosure provides a composition comprising an isolate of guarana plant and at least one of (i) an isolate of *ginkgo biloba* plant or a functional analogue thereof and (ii) fruit sugars, the composition being for use in providing an awaking effect on a subject without exhibiting a detected effect on the subject's heart activity.

In some embodiments, the composition comprising (i) an isolate of guarana plant, (ii) an isolate of *ginkgo biloba* plant or functional analogue thereof and (iii) fruit sugars.

In the following description, while reference is made mainly to compositions, it should be understood as encompassing methods making use of the compositions.

When referring to a "plant" it is to be understood to encompass the plant as a whole, as well as one or more parts thereof, including leaves, stems, seeds, flowers, fruits and roots. The plant may be subject to extraction as a fresh plant (e.g. as a whole plant) or the plant may be a priori processed by any one of drying, semi-drying, cutting, chopping, grinding, powdering and the like.

When referring to a "isolate" it is to be understood as encompassing a natural substance obtained from a plant as well as any synthetic or semi-synthetic analog thereof having a biological activity corresponding to the activity of the natural substance (the natural, synthetic or semi-synthetic isolate being regarded as active ingredient, active material, active component of the plant). In the context of the present disclosure, the isolate may be for example in a form of a plant extract. Alternatively, the isolate may be obtained from the plant by other isolation methods (not by extraction techniques).

When referring to an "extract" it is to be understood as encompassing a product of separation (or isolation) of one or more substances from a plant or a plant part using solvents. The extract is typically obtained with a water-solvent system. Plant extracts are well known in the art and may use a variety of solvents, such as, without being limited thereto, pentane, decane, cyclohexane, hexane, petroleum ether, monochloromethane, ethanol, butanol, acetone, dichloromethane, chloroform, isopropanol, propanol, ethyl acetate, methanol, butylene glycol, propylene glycol, pentylene glycol, glycerol, ethers, oils, supercritical carbon dioxide, water or any other suitable solvent, and any mixture of these solvents.

In one embodiment, the plant extract is obtained in a water-alcohol system, such as, without being limited thereto, water-ethanol system.

As noted above, each isolate (for example in the form of an extract) comprises measurable "active substances", believed to be the substances or components of the extract that are responsible for the waking effect of the final composition (namely, wakefulness). In this context it is to be appreciated that only a portion of the isolate from a plant constitutes the active substances and thus, for instance, 50 mg of an extract may include only a small fraction of active substances. The amount of active substances in an isolate may be determined by analytical methods, such as High Performance Liquid Chromatography (HPLC), chromatography, spectroscopy and the like.

When referring to "waking effect" it is to be understood as encompassing any effect improves the physical and/or mental functionality of a subject. Without being limited thereto, the term "waking effect" denotes improvement in mental capabilities such as anyone of vigilance, immediate word recall, decision making and speed of response, short memory, concentration, focus, effectiveness, increased performance, or similarly reduction in anyone of sleepiness or fatigue.

In some embodiments, the awaking effect is desirable for subject experiencing temporary reduction in the above mentioned physical and/or mental functionalities, e.g. when the subject is experiencing post lunch dip (PLD).

PLD is a phenomena associated with deterioration of function and productivity typically between noontime and 16:00. PLD is sometimes regarded as a circadian phenomenon, related with circadian rhythm of the body since it was reported to occur regardless of lunch or food intake. However, its effect may be more pronounced following lunch. PLD may be also attributed to various reasons, including, for example, hormonal (which can also be regulated by a circadian pacemaker) or nutritional/gastrointestinal changes. Another explanation for PLD may be related to body temperature changes (a decrease in the body temperature typically occurring in early afternoon hours which increases the tendency to sleep), decreased cortisone/cortisol levels, and re-distribution of blood leading to sleepiness, particularly during noon—early afternoon hours.

Thus, the present invention also provides a composition comprising (i) an isolate of guarana plant, (ii) an isolate of *ginkgo biloba* plant or functional analogue thereof and (iii) fruit sugars for use in ameliorating, inhibiting or reducing post lunch dip phenomena.

The term "ameliorating, reducing or inhibiting" as used herein, refers a complete range of positive effects of administrating to a subject a composition as disclosed herein.

By "subject" it is meant a human (at times considered patient) who may be affected by the conditions detailed herein, for example post lunch dip and the associated conditions and to whom the composition or method described herein is desired. In some embodiments, the subject being administered with the composition described herein is considered to exhibit a response to the composition.

The term "response" or "responsiveness" refers to an improvement in at least one relevant parameter after being administered with the composition as compared to a subject not being administered with the composition or as compared to the parameters of the same subject prior to administration.

The parameters of the same subject may be determined prior to administration of the composition or at any other time provided that the subject has not being administered with the composition.

In some embodiments, the parameters are associated with the "waking effect" as described herein. For example, the parameters may be an overall feeling of the subject for example an overall awaken feeling, fewer tendencies to sleep, vital feeling.

In some other embodiments, the parameters validated used function and vigilance tests. In some further embodiments, the parameters are psychomotor, cognitive or behavioral tests. In yet some further embodiments, the measured parameter is at least one of immediate word recall test (short term memory), digit symbol substitution test (concentration), and subjective rating (on a visual analogue scale—VAS) of their vigilance, ability to focus, and effectiveness at work.

As appreciated:

VAS refers to a visual-analog test in which the participant described on a line of 10 cm scale his/her subjective feeling regarding the questioned parameter. The titles in the 3 scales which were used were: somnolent—alert; confused—focused; and none-effective—effective in performance/work. Subjects were asked to cross the line according to their state at each test and the score was calculated as the length (in cm) from the left side of the line till the point that they marked. Thus, the numbers run from 0 to 10, with higher scores indicating higher subjective alertness or better performance. These scales are widely used to assess subjective complaints including somnolence, although do have some limitations.

DSST refers to the Digit Symbol Substitution Test is a time limited test in which a patient is required to replace digits by symbols in a given time restriction (2 min). The test provides data on the accuracy and rate of performing the task, and is a very common tool to assess function and compare between various sleep/alert conditions.

iWRT refers to the immediate Word Recall Test is a test of short term memory which is a very common tool to assess cognitive function and compare between various sleep/alert conditions. Thirty unrelated words were presented to the participant, each word for 2 seconds, and at the end the participant was required to recall as many words as s/he could. Both correct and incorrect or repeated words were analyzed. It has been shown to reliably quantify short term memory as a function of the frontal lobe, which can be impaired by sleepiness and improved by alertness In the context of the present disclosure an improvement in at least one of the measured parameters relates to providing an awaking effect and/or inhibiting or reducing post lunch dip. A measured improvement is defined as an improvement of at least 3%, at times at least 5%, at times at least 20%, at times even at least 50%. The measured improvement is defined as a statistically significant improvement as determined by conventional statistical tests (such as t-test).

Further in the context of the present disclosure an improvement in at least one of the parameters (including overall feeling) is considered as an improvement or response to the composition.

As detailed herein below, the composition may be administered on a need by a subject or may be administered on a daily basis.

The composition disclosed herein was found to have minimal (analysis of variance with $p<0.05$ considered statistically significant), if at all, effect on the subject's heart activity, this being compared, at least to the effect to 55 mg caffeine.

Thus, in accordance with some embodiments, the composition disclosed herein exhibits an advantageous medically negligible or no detected effect on the subject's heart activity following administration thereof to the subject.

Heart activity as used herein includes any one of the following parameters: heart rate, blood pressure, (systolic and diastolic blood pressure), etc.

When referring to a "medically negligible" or "no detected effect" it should be understood as referring to a marginal change which is statistically not significant as determined by conventional statistic tests (such as t-test) or to an effect which is below the changes that can be detected using conventional methods. In some embodiments, the heart activity is determined before consumption of the composition and compared to the activity determined after consumption of the composition in order to show the marginal or no effect on the heart activity.

In some embodiments, the heart activity is determined within a time window of up to 24 hours post administration of said composition, at times up to 12 hours post administration and at times up to 6 hours post administration.

The composition and method of the invention involves administration of an effective amount of the composition to a subject.

As used herein the term "effective amount" is intended to mean that amount of a composition, and in particular of the active components therein, that will improve the condition of the subject and in the context of the present disclosure provide "waking effect" as described herein. In some embodiments this term refers to an amount of the composition and in particular of the active components therein, which is administered to a subject in need thereof, necessary to effect a beneficial change in the condition or to reduce, inhibit or ameliorate the condition or development of the condition. In some other embodiments, the amount to be administered ameliorates, reduces or inhibits for example post lunch dip without affecting the subject's heart activity.

In some embodiments, providing or administering the composition described herein induces a positive response to the composition (or to method of administrating the composition).

In the context of the present disclosure, when referring to guarana it is to be understood as meaning *Paullinia cupana* also known by the names *Paullinia crysan*, and *Paullinia sorbilis*.

In accordance with the present disclosure, the isolate of guarana used herein, is prepared by extraction of any plant part thereof. In some embodiments, the extract is of guarana seeds. Seed extraction may be obtained by several methods known in the art. For example, seed extraction is carried out in an aqueous ethanol system after which the ethanol is evaporated and the residual guarana extract is dried. The dry extract may be hydrated prior to use. The seeds may be fresh or dry before extraction.

In some embodiments, the guarana extract is guarana seed extracts.

The amount of guarana extract in the composition may vary. In some embodiments, the composition comprises between about 30 mg guarana extract/100 ml composition to about 70 mg guarana extract/100 ml composition.

In some other embodiments, the composition comprises between about 40 mg guarana extract/100 ml composition to about 60 mg guarana extract/100 ml composition. These amounts may correspond to about 0.04% to about 0.06% (w/v) of guarana extract in the final composition.

In some embodiments, 100 ml of the composition comprises between about 45 mg to 55 mg of guarana extract, at times, between about 48 mg to 51 mg of guarana extract.

In one embodiment, 100 ml of the composition comprises about 49 mg of guarana extract.

As appreciated, the extract comprises active substances some of which are known in the art. For example, guarana and this includes guarana seeds are known to include guaranine (caffeine), tannins and saponins. In addition, guarana may include for example alkaloids such as theophylline and theobromine.

In the context of the present disclosure the active substances in guarana include without being limited herein to guaranine (caffeine), tannins, saponins and alkaloids such as theophylline and theobromine.

When referring to guaranine it should be understood to include also the other active substances disclosed herein.

As noted above, the final composition comprises between 30 to 70 mg guarana isolate. Such amount of guarana isolate from a plant provides, in some embodiments, between about 6 mg to about 20 mg guaranine in 100 ml of the final composition, at times between 7 to 17 mg guaranine in 100 ml of the final composition.

In some other embodiments, the guarana extract provides about 14 mg guaranine in 100 ml of final composition. This amount may be regarded as constituting 20% to 30% w/v of guaranine (in 100 ml final composition), at times between 24% to 29% or about 24% of guaranine (in 100 ml final composition).

In some further embodiments, the guarana isolate used here refers to guaranine prepared by synthetic methods or by modification of naturally obtained guaranine (e.g. semi-synthetic).

In accordance with the present disclosure, the isolate of *ginkgo biloba* refers to an isolate of *ginkgo biloba* or any functional analogues thereof. The term functional analogue thereof used herein denotes a substance having the same functionality as *ginkgo* in respect at least of improving oxygen circulation in the blood.

In some embodiments, the functional analogue may be selected from *Bacopa*, *Ginseng*, Huperzine A, Iodine, Alpha-lipoic acid, choline, Docosahexaenoic acid, Omega-3 fatty acids, fish oil and alpha-linolenic acid.

In some embodiments, the isolate of *ginkgo biloba* used herein, is prepared by extraction of any plant part thereof. In some embodiments, the extract is of *ginkgo biloba* leaves.

As noted above, extraction may be obtained by several methods known in the art. For example, *ginkgo biloba* leaves extract may be obtained using an ethanol/water extraction system, wherein the desired fraction of the extraction (the *ginkgo biloba* extract) is within the water fraction.

In some embodiments, the *ginkgo biloba* extract is *ginkgo biloba* leaves extract.

The amount of *ginkgo biloba* extract in the composition may vary. In some embodiments, the composition comprises between about 30 mg *ginkgo biloba* extract/100 ml composition to about 70 mg *ginkgo biloba* extract/100 ml composition In some other embodiments, the composition comprises between about 40 mg *ginkgo biloba* extract/100 ml composition to about 60 mg *ginkgo biloba* extract/100 ml composition. These amounts may correspond to about 0.04% to about 0.06% (w/v) of *ginkgo biloba* extract.

In some embodiments, 100 ml of the composition comprises between about 45 mg to 55 mg of *ginkgo biloba* extract, at times, between about 48 mg to 51 mg of *ginkgo biloba* extract.

In one embodiment, 100 ml of the composition comprises about 49 mg of *ginkgo biloba* extract.

As appreciated, the extract comprises active substances some of which are known in the art. For example, *ginkgo biloba* and this includes *ginkgo biloba* leaves are known to include flavonoid glycosides and terpenoids (ginkgolides, bilobalides). In accordance with one embodiment, the amount of flavonoid glycosides is determined as the amount of active substances in the *ginkgo biloba* extract. The amount may be determined using, for example, HPLC.

As noted above, the final composition comprises between 30 to 70 mg *ginkgo biloba* extract. Such amount of *ginkgo biloba* extract provides, in some embodiments, between about 6 mg to about 20 mg flavonoid glycosides in 100 ml of the final composition, at times between 7 to 17 mg flavonoid glycosides in 100 ml of the final composition.

In some other embodiments, the *ginkgo biloba* extract provides about 11 mg flavonoid glycosides in 100 ml of final composition. This amount may be regarded as constituting between 20% w/v to 30%, at times between 24% to 29% or about 24% of flavonoid glycosides (in 100 ml final composition).

As appreciated, various flavonoid glycosides may be found in plants and these include, without being limited thereto, hesperidin, naringin, rutin and quercitrin.

In some other embodiments, the isolate of *ginkgo biloba* comprises synthetic flavonoid glycosides.

In accordance with another aspect, the present invention provides a composition comprising guaranine and at least one of (i) flavonoid glycosides or terpenoids and (ii) fruit sugars. In some embodiments, the composition comprises in 100 ml final composition between about 6 mg to about 20 mg guaranine and between about 6 mg to about 20 mg flavonoid glycosides.

The composition of the present disclosure may comprise for example guarana isolate from plant and synthetic flavonoid glycosides or visa versa, namely synthetic guaranine and flavonoid glycosides isolate from plant.

In some embodiments, in a 100 ml composition the following amounts are included: (i) between about 6 mg guaranine to about 20 mg guaranine (at times between 7 to 17 mg); (ii) between about 6 mg to about 20 mg flavonoid glycosides (at times between 7 to 17 mg); and (iii) between about 4 ml to about 15 ml fruit sugars.

While it is known that *ginkgo biloba* provides nutritional support for mental alertness, short and long term memory, increase reaction time, improved mental clarity, enhance vitality level, improve circulatory health and blood vessel health, its combination with guarana at the amounts provided herein, and in the absence of high amounts of caffeine or other acceptable stimulants (amount above 50 mg/100 ml), exhibited superiority over compositions comprising such amounts of stimulants. In the absence of high amounts of caffeine or the like, the compositions disclosed herein are regarded as being "essentially free of stimulant". The term "essentially free of stimulant" is used herein to denote that the amount of stimulants, such as caffeine and/or taurine in the composition is not more than 10% w/v of the final composition (out of 100 ml final composition).

When referring to "stimulants", it is to be understood as denoting any substance known to improve mental or physical function of a subject as described above. Non-limiting examples of stimulants include, without being limited thereto are caffeine and taurine, Vitamin B Complex.

Caffeine is the most common stimulant found naturally in coffee, tea and is widely used in soft drinks specifically in larger amount in energy drinks. It is known to be useful as a cardiac stimulant and a mental stimulant. One drawback in using caffeine resides in its effect in increasing heart pulse rate and blood pressure. In addition, regular coffee drinking results in tolerance and substantial reduction of the effect of caffeine. Taurine is considered as a similar stimulant.

Also included in the final composition disclosed herein are fruit sugars. These include natural fruit sweetener extracted entirely from fruits. In some embodiments, the fruit sugars are selected as those having a low glycemic index.

In some embodiments, the natural fruit sweetener is extracted from apples, grapes, pear, pineapple, orange, peach etc. Such extracts are known to have a Brix level of between 60° Bx to 80° Bx (at 20° C.). The fruit sugars may be added to the composition in the form of crystal sugar or sugar syrups. This may be obtained by adding to the final composition an amount constituting between about 4% to about 15% fruit sugar. In some other embodiment, the composition comprises between about 6% to about 10% fruit sugars. In some further embodiments, the composition comprises between about 7% to about 8% fruit sugars (corresponding to between 6 to 10 ml fruit sugars in 100 ml final composition).

In some embodiments, the fruit sugars are commercially available, such as the commercial all natural fruit sweetener product known as Fruit-up® (WILD Valencia S.A).

In some embodiments, the composition may also comprise additional plant derives substances.

In one embodiment, the composition comprises an extract of elderberry, in particular, the berry of the black elder tree (*Sambucus nigra*) and this provides a source of vitamins A, B and C, bioflavonoids and anthocyanins. Extraction from the berry may be performed by any known technique. In accordance with some embodiments, the extraction is performed using an ethanol/water extraction system. The extract is the fraction soluble in water.

According to some embodiments, elderberry extract is included in the final composition in an amount between about 0.04% to about 0.06% (v/w).

In some embodiments, the elderberry extract was added in an amount between about 0.04% to about 0.05% (v/w).

In some embodiments, the final composition comprises between 40 mg to 60 mg of elderberry extract (in 100 ml final composition), at times, in an amount of about 49 mg of elderberry extract in 100 ml final composition.

In some embodiments, the active substance in the elderberry comprises anthocyanins and the amount of anthocyanins in the elderberry extract may be between 1% to 5%, at times between 2% to 4%. In some embodiments, the elderberry extract comprises 3% of anthocyanins. Anthocyanins are found in different plant parts such as leaves, stems, roots, flowers and fruits. Anthocyanins consist of a backbone known as anthocyanidin which is bound to one of three sugars: arabinose, glucose, or galactose.

The composition may comprise additional ingredients such as one or more of artificial sweeteners, minerals, vitamins (such as Vitamin A, Vitamin B1, Vitamin B2, Vitamin B6, Vitamin B12, Vitamin C, Vitamin D3, Vitamin E, Folic Acid). The composition may comprise flavoring agents such as these that may provide for example a lemon taste.

The composition disclosed herein was found to be superior over consumption of 50 mg caffeine. While the composition and consumption of 50 mg caffeine may be regarded as providing a similar waking effect, it is clearly exhibited herein (in the following non-limiting examples) that caffeine affected heart rate and blood pressure to an extent that was not observed by the composition disclosed herein.

The composition disclosed herein was found to be suitable for daily dose, as the subjects being given the composition on a daily basis did not develop tolerance to the composition and at times showed even a favorably accumulating effect (e.g. beneficial awaking effect) of the composition.

Specifically as shown in Example 5 herein below, consumption of the composition for a time period of 30 days resulted in an improvement in the validated used function and vigilance tests as detailed herein.

In addition, consumption of the composition for 30 days led to an improvement in the baseline measured. Without being bound by theory it was suggested that the improvement may be attributed to an accumulative effect of the composition.

Interestingly and in contrast to caffeine consumption, the composition was well tolerated for the tested time period.

Thus, in accordance with another aspect, the present invention provides a composition comprising (i) an isolate of guarana plant, (ii) an isolate of *ginkgo biloba* plant or functional analogue thereof and (iii) fruit sugars for use in ameliorating, inhibiting or reducing post lunch dip, wherein the composition is for use as a daily dose during a period of at least 7 days.

In some other embodiments, the composition is for use during a period of at least fourteen days. In some further embodiments, the composition is for use during a period of at least thirty days.

In some other embodiments, the composition is for use once or twice a day. In some further embodiments, the composition is for use once a day.

Consumption (use, administration, providing) of the composition of the developed composition may be in general at any time of the day. In some embodiments, the composition is for use during or before post lunch dip is developed. In some other embodiments, the composition is for use before noon or within a time window of up to an hour before post lunch is developed in a subject in need thereof.

In some embodiments, the composition disclosed herein may be provided as a drink, such as an energy drink. For example, the energy drink may be used prior to lunch and may assist in post lunch dip. In some other embodiments, the composition may be used as a beverage. In some other embodiments, the composition may be mixed with other liquids, such as water, flavoring materials, natural juices, etc.

In some other embodiments, the composition may be provided in tablet form, wherein the ingredients are compressed together with microcrystalline cellulose into a tablet. The tablet may be in a form suitable for dissolution in water or any other liquid suitable for human consumption.

DETAILED DESCRIPTION ON SOME NON-LIMITING EXAMPLES

Example 1 Preparation of Various Compositions

Methods:

The ingredients were mixed where the fruit sugars (polysaccharides) are first dissolved by mixing with water at 25-35° C. for at least 20 minutes. Then, remainder of the components are added while mixing for an additional period of 30 min. Alternatively, sorbate, plants extracts and stabilizers are mixed in 10% of the water prior to the addition of the sugars. At times, mixing is under high sheer forces.

Results:

The following compositions were formulated:

TABLE 1

Components of Composition 1

| Ingredient | Amount in 100 ml | |
|---|---|---|
| | liquid (ml) | powder (g) |
| Water (Superherb, Israel) | 82 | |
| Fruit up (Wild) | 8 | |
| Pectin (HF 102) (Shavit, Israel) | | 0.25 |
| Xantham Gum (Shavit, Israel) | | 0.02 |
| Apple concentrate (Black & Decker) | | 10 |
| Vitamin C (Shavit, Israel) | | 0.03 |

TABLE 1-continued

Components of Composition 1

| Ingredient | Amount in 100 ml | |
|---|---|---|
| | liquid (ml) | powder (g) |
| Apple flavor (Wild) | 0.08 | |
| Berries flavor (Wild) | 0.09 | |
| Black carrot (Wild) | 0.024 | |
| Citric acid (anhydrous) (Shavit, Israel) | | 0.1 |
| Sorbate (Shavit, Israel) | | 0.2 |
| Guarana extract (FIC NatuRx) | | 0.063 |
| Elderberry extract (FIC NatuRx) | | 0.05 |
| Ginkgo extract (FIC NatuRx) | | 0.05 |

TABLE 2

Components of composition 2

| Ingredient | % in 100 ml |
|---|---|
| Water (Superherb, Israel) | 88.397 |
| Fruit up sugar (WILD) | 7.887 |
| Liquid Sucralose (Black & Decker) | 1.183 |
| Grapefruit Concentrate (Black & Decker) | 0.986 |
| Citric Acid (Shavit, Israel) | 0.493 |
| Powder Natural Orange Flavour (WILD) | 0.394 |
| Potassium Sorbate (Shavit, Israel) | 0.197 |
| Liquid Natural Lime flavor (WILD) | 0.197 |
| Liquid Natural Grapefruit flavor (WILD) | 0.089 |
| Elderberry Extract (FIC NatuRx) | 0.049 |
| Guarana Extract (FIC NatuRx) | 0.049 |
| Ginkgo Extract (FIC NatuRx) | 0.049 |

TABLE 3

Components of composition 3 ("Wakeup")

| Ingredient | % in 100 ml |
|---|---|
| Water (Frutarom, Israel) | 87.5 |
| Fruit up sugar (Wild) | 7.9 |
| Sugar (Frutarom, Israel) | 4.0 |
| Sucralose (Frutarom, Israel) | 0.0075 |
| Citric Acid (Frutarom, Israel) | 0.35 |
| Potassium Sorbate (Frutarom, Israel) | 0.02 |
| Xantham Gum (Frutarom, Israel) | 0.03 |
| Elderberry Extract (FIC NatuRx) | 0.049 |
| Guarana Extract (FIC NatuRx) | 0.049 |
| Ginkgo Biloba Leaf Extract (FIC NatuRx) | 0.049 |
| Masking Nat (Frutarom, Israel) | 0.030 |
| Lemon Grass (Frutarom, Israel) | 0.02 |

TABLE 4

Components of composition 4 (caffeine composition)

| Ingredient | Amount in 100 ml | |
|---|---|---|
| | Liquid (ml) | Powder (gram) |
| water | 82 | |
| Glucose | 8 | |
| Pectin | | 0.25 |
| Xantham Gum (Shavit, Israel) | | 0.02 |
| Apple concentrate (Black & Decker) | | 10 |
| Apple flavor (Wild) | 0.08 | |
| Berries flavor (Wild) | 0.09 | |
| Black carrot (Wild) | 0.024 | |
| Citric acid (anhydrous) | | 0.1 |
| Sorbate (Shavit, Israel) | | 0.2 |
| Caffeine (Superherb, Israel) | | 0.050 |

TABLE 5

Components of composition 5 (Placebo)

| Ingredient | Amount in 100 ml | |
|---|---|---|
| | Liquid (ml) | Powder (gram) |
| water | 82 | |
| Glucose | 8 | |
| Pectin | | 0.25 |
| Xantham Gum (Shavit, Israel) | | 0.02 |
| Apple concentrate (Black & Decker) | | 10 |
| Apple flavor (Wild) | 0.08 | |
| Berries flavor (Wild) | 0.09 | |
| Black carrot (Wild) | 0.024 | |
| Citric acid (anhydrous) | | 0.1 |
| Sorbate (Shavit, Israel) | | 0.2 |

Example 2—Sensory and Consumer Study

Method:

The study population included 98 adults (ages 25 to 35), 60% men and 40% women with 68% out of the total population having an academic degree.

Each participant was provide with 4 drinks of composition 1 and was requested to drink one drink after lunch for a time period of 4 days and a list of questions. Participants' remarks on questions were monitored after 4 days of drinking the formulation.

Figure 1B:
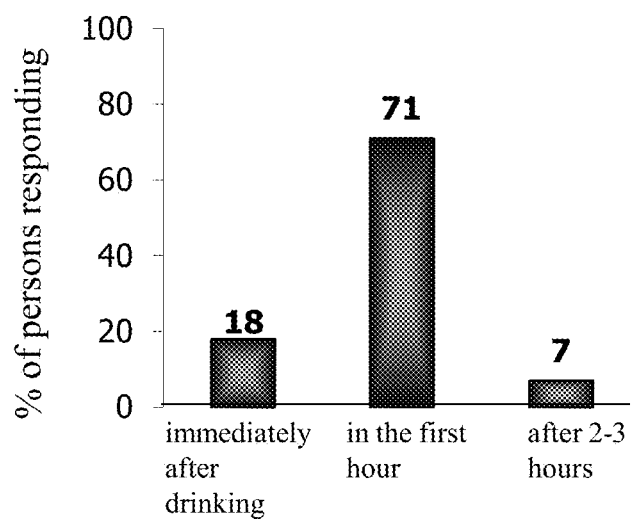

Results:

The results of this study obtained with composition 1 indicated that drinking the formula after lunch, 71% of the participants reported that they felt awake one hour after drinking the formula (FIG. 1A). 66% reported that awakens was preserved for a time period of 2-3 hours (FIG. 1B).

Example 3 Clinical Studies

Methods:

A group of thirty healthy non smoker volunteers (13 male, 17 female) was recruited to the test via advertisements in the faculty of medicine. The volunteers had an average age of 36.6±12.4 years (range 18-61) and an average BMI value of 24.3±3.5 Kg/m2 (range 17.0-31.8). They were all in stable medical condition, free of chronic diseases or medications.

In the first study visit they were given explanations on the study, signed the consent form, and were trained with the performance tests. Thereafter, the study consisted of 3 additional visits, with 6±3 days between each 2 study visits. All 3 study visits were performed in a similar fashion, on identical time of the day, as described below.

In each visit volunteers had a standard lunch between 12:00-13:00, including for example meat, fish, rice, vegetables, or a vegetarian dish with no desert. After lunch, each volunteer drank either composition 2 (tested formula), 50 mg caffeine (composition 4, Caffeine control composition) or placebo (composition 5) in a cross over double blind regimen. All three drinks had a similar look and taste, and were in a similar bottle containing 100 ml volume.

Volunteers were asked to maintain a stable and regular schedule, and maintain a stable sleep/wake regimen during the study period. They were asked to maintain a stable time in bed and daytime activity during the period of the study. Specifically they were asked to go to bed and wake up in the morning at the same times before and in the days of the study visits. They were also asked to maintain a similar breakfast in all three mornings of study visits.

Each visit had the same routine: participants had a lunch and immediately after it they drank 100 ml of composition 2, composition 4 (caffeine) or composition 5 (placebo).

Each volunteer was tested 30 min and 120 min following drinking, by measuring vital signs, blood pressure, and validated commonly used standard function and vigilance tests such as an immediate word recall test (short term memory), digit symbol substitution test (concentration), and subjective rating (on a visual analogue scale—VAS) of their vigilance, ability to focus, and effectiveness at work.

The results of the three visits were compared utilizing one way analysis of variance, with $p<0.05$ considered statistically significant.

This study was approved by the institutional review board (IRB, Helsinki committee) of Rambam Medical Center and all participants have signed an informed consent prior to participation.

Psychomotor/Cognitive and Behavioral Tests Utilized in the Study:

VAS—a visual-analog test in which the participant described on a line of 10 cm scale his/her subjective feeling regarding the questioned parameter. The titles in the 3 scales which were used were: somnolent—alert; confused—focused; and none-effective—effective in performance/work. Subjects were asked to cross the line according to their state at each test and the score was calculated as the length (in cm) from the left side of the line till the point that they marked. Thus, the numbers run from 0 to 10, with higher scores indicating higher subjective alertness or better performance. These scales are widely used to assess subjective complaints including somnolence, although do have some limitations.

DSST—the Digit Symbol Substitution Test is a time limited test in which a patient is required to replace digits by symbols in a given time restriction (2 min). The test provides data on the accuracy and rate of performing the task, and is a very common tool to assess function and compare between various sleep/alert conditions.

iWRT—immediate Word Recall Test is a test of short term memory which is a very common tool to assess cognitive function and compare between various sleep/alert conditions. Thirty unrelated words were presented to the participant, each word for 2 seconds and at the end the participant was required to recall as many words as s/he could. Both correct and incorrect or repeated words were analyzed. It has been shown to reliably quantify short term memory as a function of the frontal lobe, which can be impaired by sleepiness and improved by alertness.

Results:

All volunteers completed the study. Two participants suffered from dizziness after drinking the composition containing 50 mg caffeine. No side effects or complaints have observed following drinking compositions 2 or 5, namely the tested formula and the placebo.

Figure 2A:
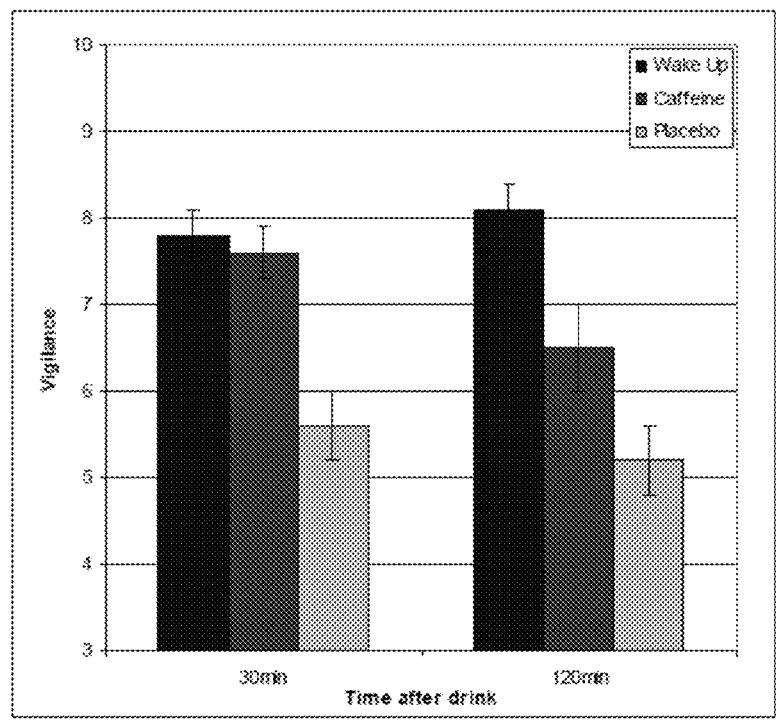
FIGS. 2A-2E are bar graphs showing the effects of composition 2 ("wake up") on the vigilance rating (VAS, FIG. 2A), on the focus ability (FIG. 2B), on the effectiveness at work (FIG. 2C), on the immediate correct words recall test (FIG. 2D) and on the number of correct symbols in the digit symbol substitution test (DSST, FIG. 2E).
Figure 2B:
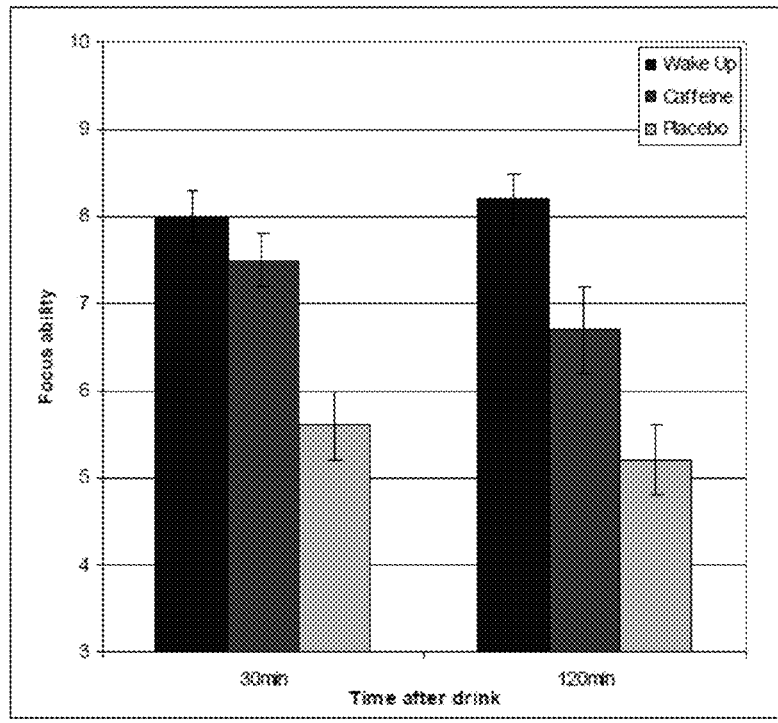
Figure 2C:
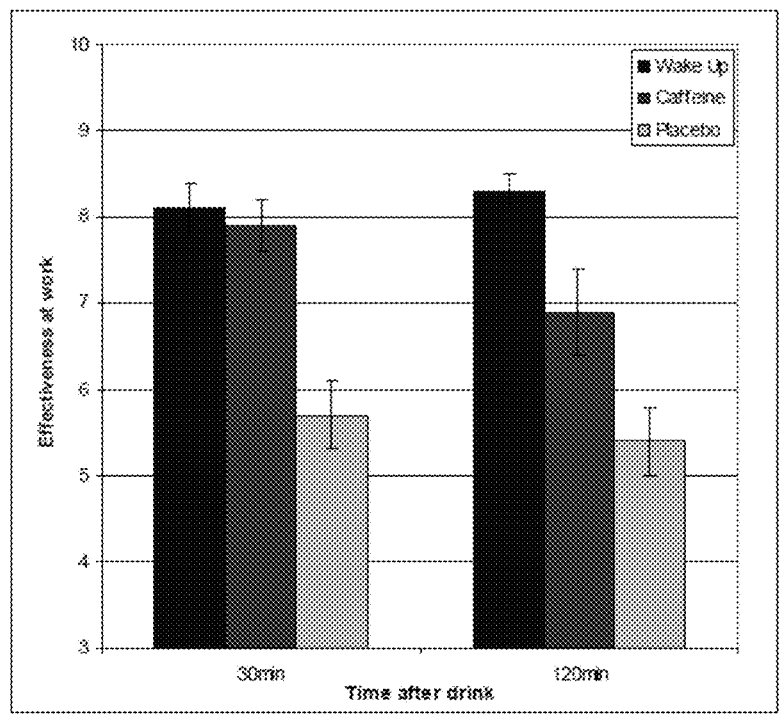

In all performance tests and subjective vigilance and effectiveness assessment, the results obtained after drinking both composition 2 or 5 (tested composition and caffeine-control composition) were significantly better 30 min following lunch compared with placebo. However, 2 hours following lunch, the effect of the tested formulation was maintained while the effect caffeine containing drink was deteriorated (FIGS. 2A, 2B and 2C).

As can be seen, 30 min after drinking compositions 2 and 5 there was a significant improvement. However, 2 hours following drink there was a deterioration of the self rating following caffeine (in all 3 dimensions), and only following "Wake up" vigilance and performance remained high.

Figure 2D:
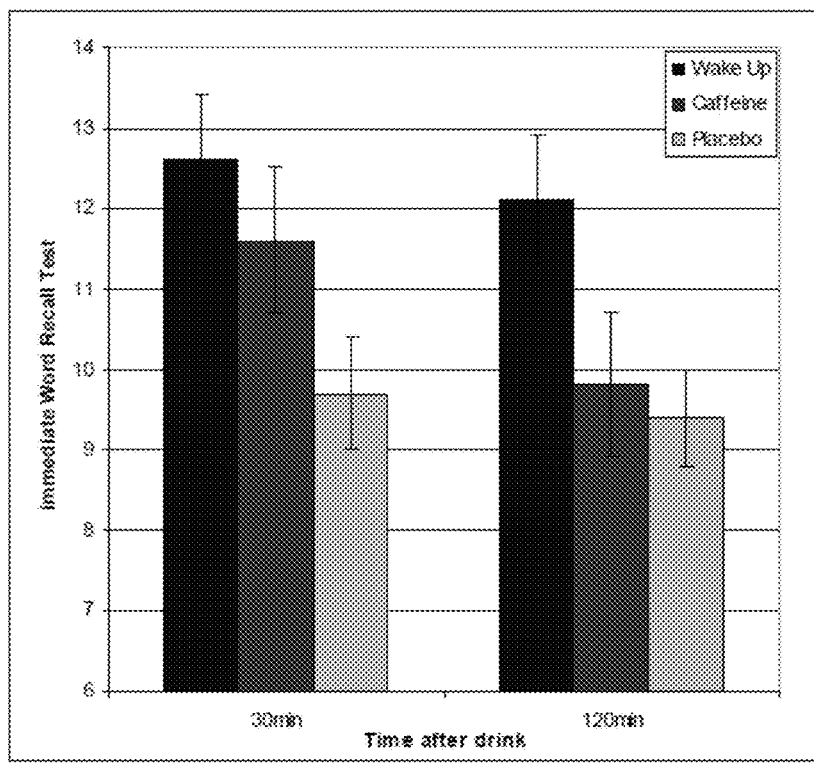

As can be seen in FIG. 2D, the number of correct words recalled 30 min after drinking was somewhat similar between the group drinking the formula and the ones drinking caffeine (12.6±4.1 and 11.6±4.8, respectively) significantly better (p<0.05) compared with the group drinking the placebo drink (9.7±3.8).

However, 2 hours following the drinking, the number of words recalled was significantly higher (12.1±4.3) in the group drinking formula compared with the groups drinking either caffeine or placebo (9.8±4.9 and 9.4±3.5, respectively) (FIG. 2D).

Figure 2E:
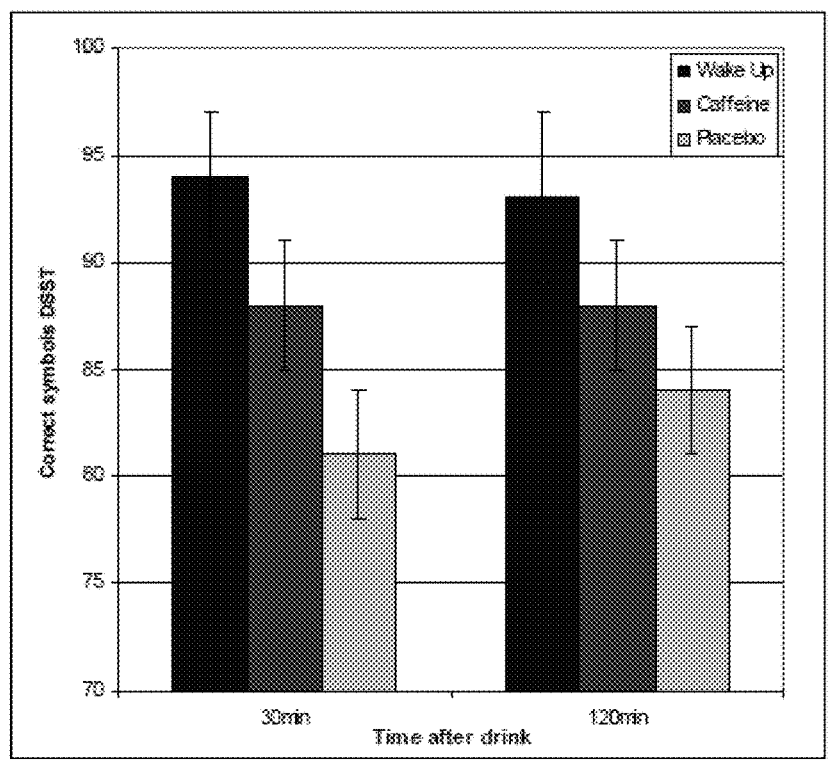

FIG. 2E shows that the number of correct symbols 30 min and 120 min after drinking was obtained in the group drinking the tested formula both after 30 min and 120 min after drinking.

The pulse rate and blood pressure, measured 30 min after drinking, were significantly higher following drinking caffeine compared to the tested formula: 77.4±1.9/min vs. 71.9±1.8/min and 119/75 vs. 113/71 mmHg, p<0.05. Two hours after drinking the values of these two parameters were similar in the three groups.

These results indicate that drinking the tested formula after lunch improves vigilance and performance 30 min after drinking, same as caffeine and significantly better than placebo. When tested 120 min after drinking, performance and vigilance in the group drinking the tested formula remains significantly higher than both placebo and caffeine. While Caffeine was associated with increasing pulse and blood pressure 30 min after drinking, in the group drinking the tested formulas no hemodynamic differences were observed compared with placebo, both 30 min and 120 min after drinking.

Example 4—Clinical Studies

Methods:

A group of 20 healthy volunteers (10 male, 10 female) was recruited to the test. The volunteers had an average age of 37±11 years (range 19 to 63), an average height of 170 cm and average weight of 73 Kg.

Lunch was provided between 12:00 to 13:00 and immediately thereafter the volunteers were examined (time "0"). The volunteers then drank composition 3 ("Wakeup" composition) and were examined again 30 min and 120 min after drinking.

Each volunteer was tested by measuring pulse, blood pressure, and validated commonly used standard function and vigilance tests such as an immediate word recall test (short term memory, IWRT), digit symbol substitution test (concentration, DSST), and subjective rating (on a visual analogue scale—VAS) of their vigilance, ability to focus, and effectiveness at work.

Figure 3A:
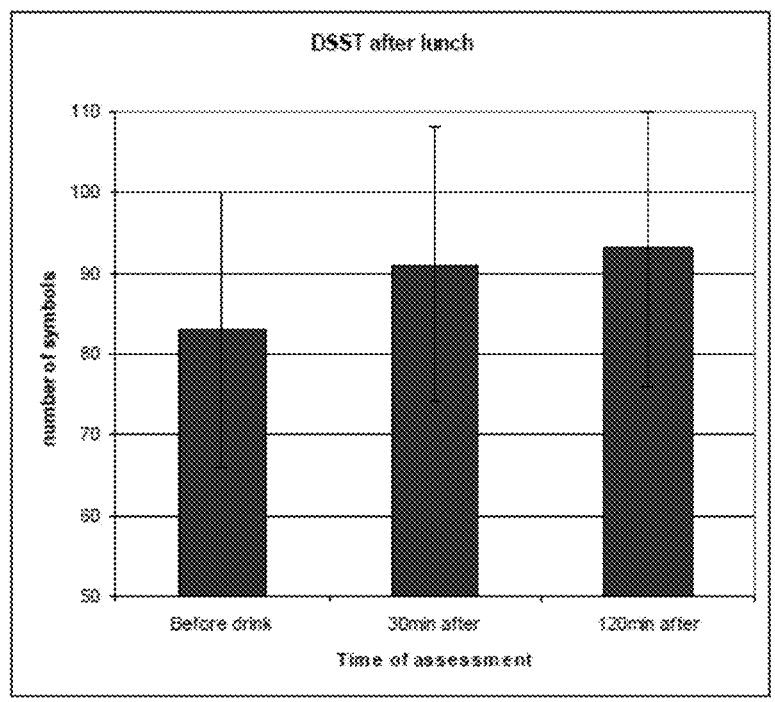
FIGS. 3A-3D are bar graphs showing the effect of composition 3 on the correct symbols in the DSST (FIG. 3A), on the vigilance (FIG. 3B), on the focus ability (FIG. 3C), and on the immediate word recall test (FIG. 3D).
Figure 3B:
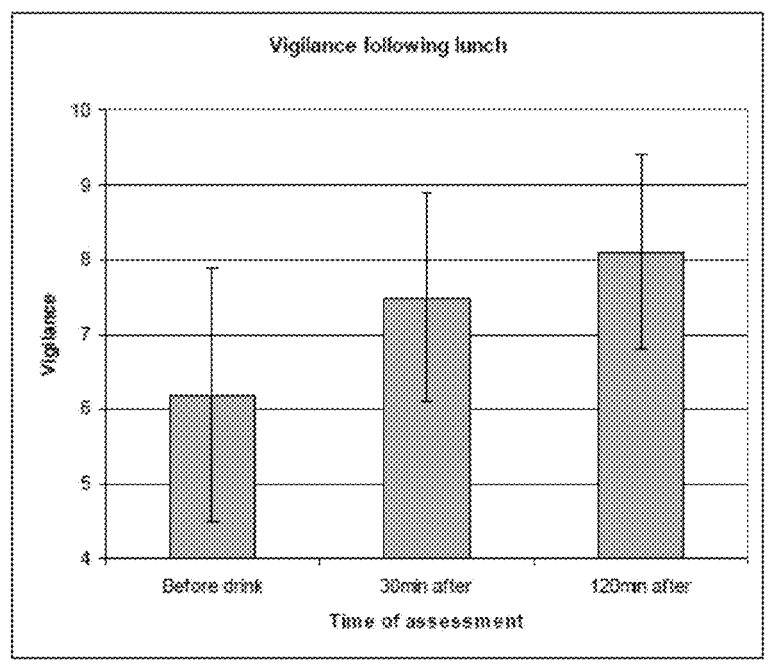
Figure 3C:
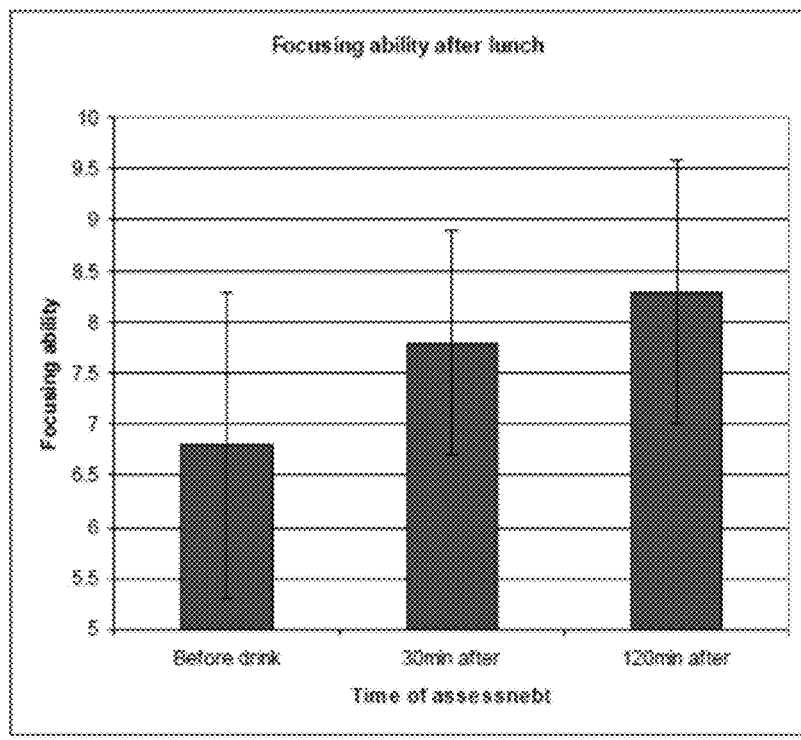
Figure 3D:
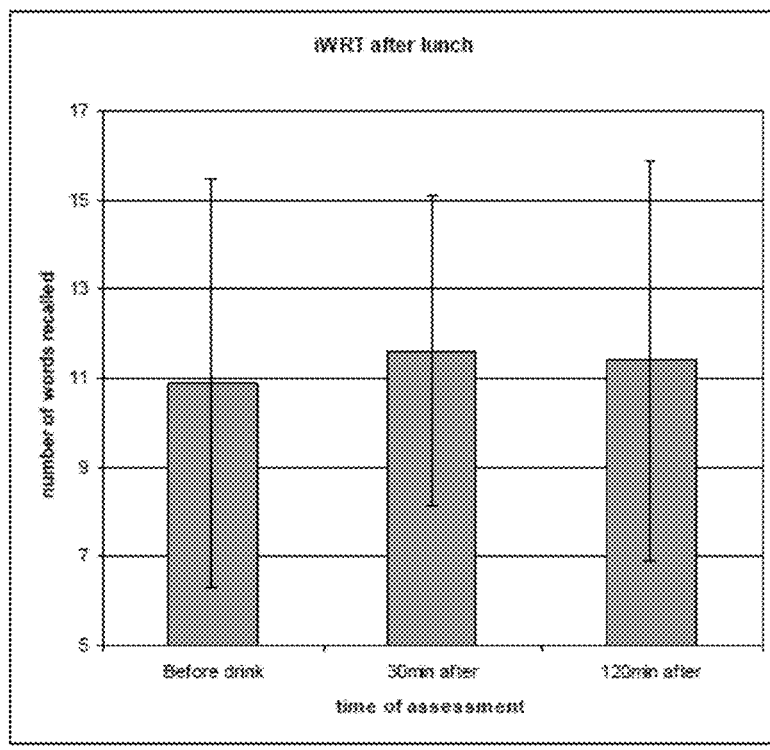
Figure 4A:
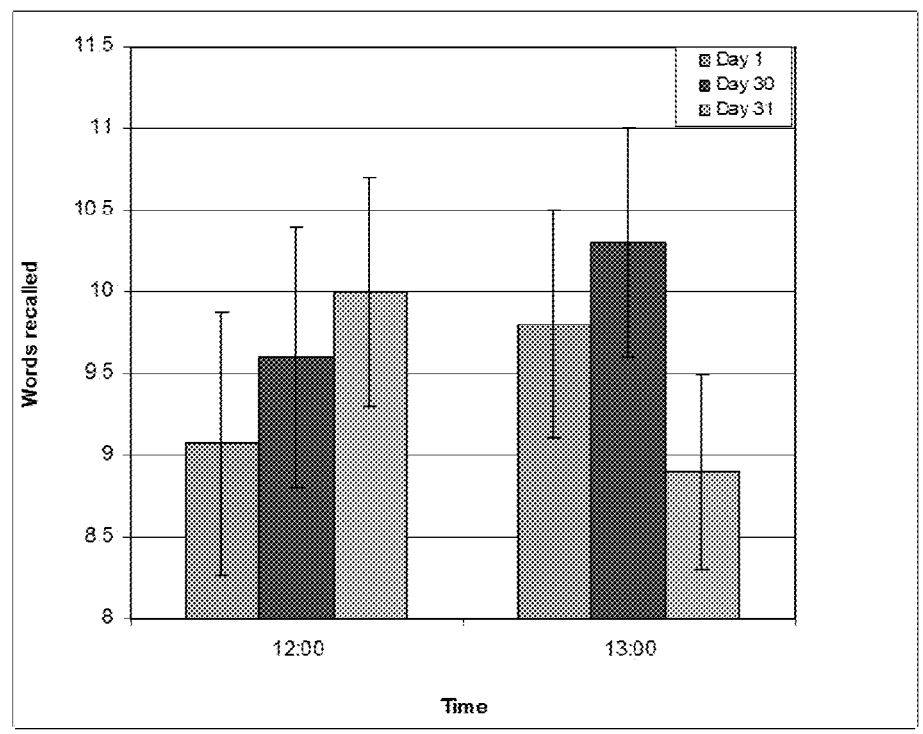
FIGS. 4A-4D are bar graphs showing the effect of daily dosing of composition 3 on the immediate word recall test (FIG. 4A), on the correct symbols in the DSST (FIG. 4B), on the vigilance (FIG. 4C), and on the work effectiveness—VAS scores (FIG. 4D).
Figure 4B:
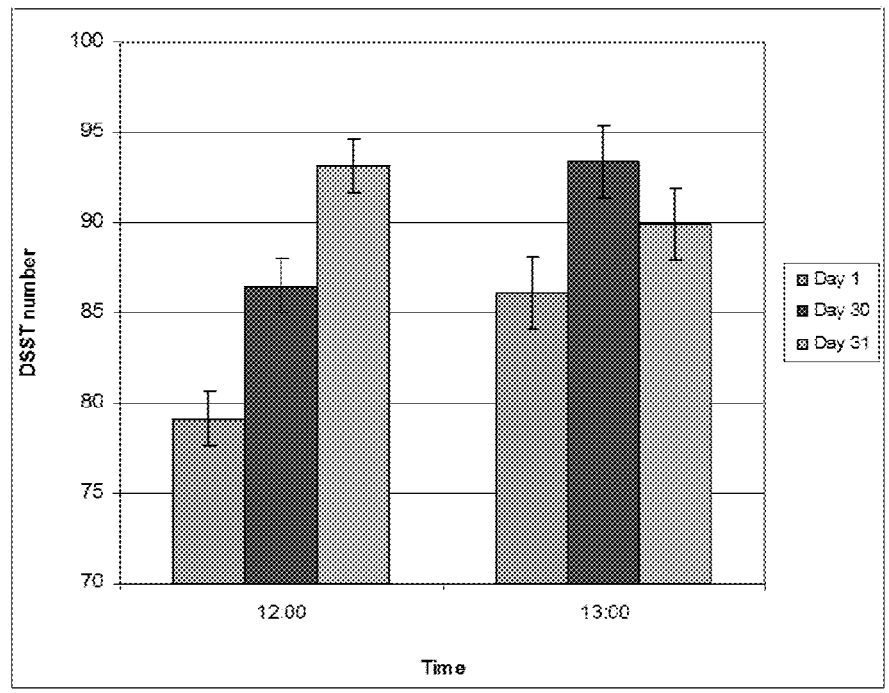
Figure 4C:
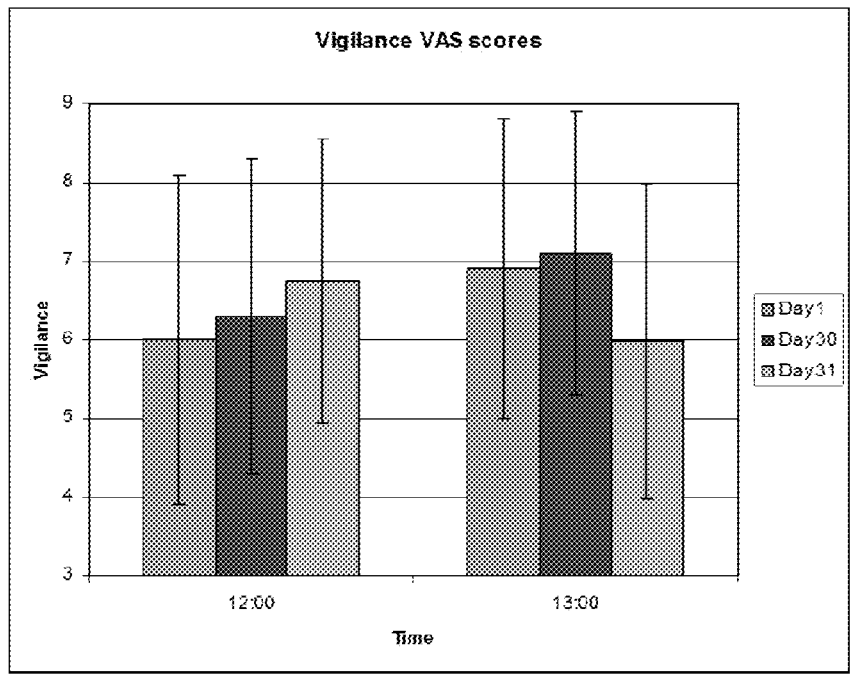
Figure 4D:
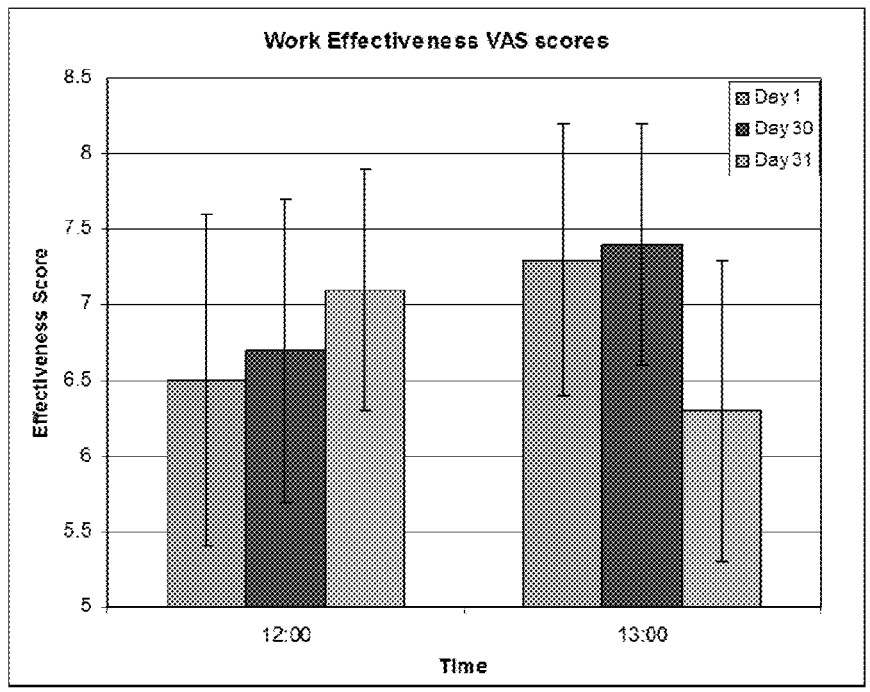

Results:

A statistically significant improvement in the capability of switching numbers of symbols (FIG. 3A), in the vigilance (FIG. 3B) and on the focus ability (FIG. 3C) was observed 3o min and 120 min after drinking the composition. In addition, the number of correct words recalled 30 min after drinking was also enhanced after drinking the composition (FIG. 3D).

The pulse rate and blood pressure, measured 30 min and 120 minutes after drinking were almost unaffected by drinking the composition.

Therefore, based on these results it appears that the tested composition (Wakeup composition 3) is effective in counteract the somnolence and reduced performance during the post lunch hours.

Example 5—Clinical Studies—Long Term Administration

As shown above, individual who drank composition 3 were observed with a significant improvement in the capability of switching numbers of symbols, in the vigilance and in the focus ability, without any observed increase in the blood pressure and pulse rate.

The objectives of this study were to evaluate the effects of composition 3 on individuals who were provided with this composition on a daily basis for a month.

Methods:

A group of ninety five healthy volunteers above 18 years old were recruited to the test.

Measurements were conducted at three different time points: the first measurement was on the first day of the study that included drinking composition 3 (Wakeup) ("day 1"), the second measurement was on the last day of the study, namely day 30 of the study ("day 30"), and the third measurement was on the next day after the second measurement, namely in the first day without drinking after the 30 days of drinking ("day 31").

On day 1 and day 30 of the study the volunteers reported to the hospital at 11:45 (before noon) and had a standard lunch as detailed above.

Immediately after lunch on both measurement days, the volunteers underwent a battery of functional tests and hemodynamic measurements (as detailed below), and then drank one bottle of composition 3 (100 cc). After an hour (at about 13:00) the volunteers underwent a repeated battery of the same tests.

Volunteers continued to drink composition 3 on daily basis immediately after lunch for a month. Namely, a total of 29 days between the first measurement (day 1) and the second measurement (day 30). Thus, volunteers drank composition 3 without reporting to the hospital between day 2 and day 29 of the study and overall drank composition 3 for 30 days.

On day 31 of the study the volunteers had the same regimen, namely reported to the hospital at 11:45 had lunch and tested at 12:00 and again at 13:00. The only difference on this day (day 31) was that the volunteers did not drink composition 3 after lunch.

The Volunteers were examined by a battery of tests consisted of measurement of vital signs, blood pressure, blood rate and validated commonly used standard function and vigilance tests such as an immediate word recall test (short term memory), digit symbol substitution test (concentration), and subjective rating (on a visual analogue scale—VAS) of their vigilance, ability to focus, and effectiveness at work.

In each visit (day 1, day 30 and day 31) the results of the tests conducted at 12:00 and at 13:00 were compared to each other in order to evaluate the effect of drinking composition 3.

In addition the results of the tests on the three days of visit (day 1, day 30, day 31) were compared to each other, utilizing either paired t-test or one way analysis of variance, with p<0.05 considered statistically significant.

Results:

The study was approved by the institutional review board (IRB, Helsinki committee) of Rambam Medical Center and all participants have signed an informed consent prior to participation.

Overall, ninety-five volunteers (40 males and 55 females) participated in this study. Their average age was 37±11 years (range 19-63 years), and their average BMI was 24.5±1.7 Kg/m$^2$ (range 19.7-34.7).

The results of their functional tests before and following the drink on day 1, day 30, and day 31 are presented in Table 6. As detailed above, the volunteers did not drink composition 3 on day 31.

As can be seen, in the first day drinking composition 3 resulted in an overall improvement in all the tested parameters. An objective improvement (iWRT and DSST) of about 8.5% and a subjective improvement (Vigilance, focusing and effectiveness) of about 14% were observed.

On day 30, drinking composition 3 resulted in an overall objective improvement of 7.3% and subjective improvement of about 11.5%.

On day 31, at which the volunteers only reported to the hospital but did not drink composition 3, the results of the objective tests deteriorated by 7.1%, and the subjective VAS measures deteriorated by about 11.7%.

Interestingly, a gradual baseline improvement in the results of the various tests was observed (Table 6, FIG. 4).

Word recalled at baseline increased from day 1 to day 30 by 5.5% and further increased in day 31 by additional 4.2 percent. Similarly DSST score increased from a baseline of 79 in day 1 to 87 in day 30 (rise of 10%) and to 93 in day 31 (additional rise of 6.9%). There was a similar trend in the VAS scores for vigilance, focusing and effectiveness (rises of 5-7% from the baseline of day 1 to the baseline of day 30, and a further rise of 6-7.5% to day 31). These data are presented in FIGS. 1-4 (left panel, at 12:00) and in Table 6.

The hemodynamic measures at the various times are presented in Table 7. As can be seen, drinking composition 3 did not result in any significant change in blood pressure or pulse rate. The reduction of 0.4-2.5% in pulse rate and blood pressure following drinking composition 3 probably reflects the post lunch dip phenomenon, as is also seen on Day 31.

This clinical current study shows that without drinking composition 3, a post lunch dip phenomenon is observed on Day 31. Namely there is deterioration in the tested parameters after lunch. This is indicted by the reduction in the objective performance tasks by 7.1% and subjective alertness, focusing ability and work effectiveness by 11.2-11.9%. Pulse and blood pressure dropped by an average of 2.4%.

However, drinking composition 3 immediately after lunch these drops are not only blocked, but there an improvement is observed in both objective test performances and in subjective assessment of alertness, focusing ability and work effectiveness. The magnitude of these improvements ranged on day 1 between 8-14.9 percent.

Thus, given the expected drop in these parameters due to post lunch dip, the net effect of the drinking composition 3 seems to be close to 20%. Furthermore, this study demonstrates that a daily use of the composition over 30 days (one bottle of 100 cc per day) does not result in tolerance or habituation, since the improvements observed in day 30 are similar to those observed in day 1, and range between 6.6-12.8 percent.

Importantly, these effects throughout the entire study did not adversely affect hemodynamic measures.

Finally, surprisingly, even baseline scores before drinking improved between Day 1 and Day 30 (by about 8%), and further improved on Day 31 (additional improvement of about 5%).

Without being bound by theory, it may be suggested that this may be associated with accumulative additive long term effect of the composition. This hypothesis is supported by the fact that subjective VAS is probably not associated with a learning curve.

TABLE 6

Effect of daily administration of Composition 3 on physicomotorcognitive and behavioral tests

| | Day 1 | | | Day 30 | | | Day 31 | | |
|---|---|---|---|---|---|---|---|---|---|
| | Before WU | 1 h after WU | Change (%) | Before WU | 1 h after WU | Change (%) | After Lunch | 1 h after Lunch | Change (%) |
| iWRT | 9.1 ± 3.7 | 9.8 ± 3.4 | +8.0 | 9.6 ± 3.9 | 10.3 ± 3.9 | +6.6 | 10.0 ± 3.8 | 8.9 ± 3.3 | −10.8 |
| DSST | 79 ± 14 | 86 ± 15 | +8.9 | 87 ± 15 | 93 ± 16 | +8.0 | 93 ± 17 | 90 ± 19 | −3.5 |
| Vigilance | 5.9 ± 2.1 | 6.9 ± 1.9 | +14.9 | 6.3 ± 2.0 | 7.911.8 | +12.8 | 6.7 ± 1.8 | 6.0 ± 2.0 | −11.2 |
| Focusing | 6.0 ± 1.9 | 6.9 ± 1.8 | +14.8 | 6.3 ± 2.0 | 7.1 ± 1.9 | +11.4 | 6.8 ± 1.7 | 6.0 ± 2.0 | −11.9 |
| Effectiveness | 6.4 ± 1.9 | 7.3 ± 1.3 | +12.5 | 6.7 ± 2.0 | 7.4 ± 1.8 | +10.4 | 7.1 ± 1.6 | 6.3 ± 2.0 | −11.9 | iWRT = immediate Word Recall Test;
DSST = Digit Symbol Substitution Test.
WU = WakeUp ® composition 3.

TABLE 7

Effect of daily administration of Composition 3 on heart activity

| | Day 1 | | | Day 30 | | | Day 31 | | |
|---|---|---|---|---|---|---|---|---|---|
| | Before WU | 1 h after WU | Change (%) | Before WU | 1 h after WU | Change (%) | After Lunch | 1 h after Lunch | Change (%) |
| Pulse | 74 ± 11 | 73 ± 10 | −0.4 | 77 ± 10 | 75 ± 11 | −2.5 | 76 ± 11 | 73 ± 11 | −3.5 |
| Systolic BP | 122 ± 12 | 120 ± 13 | −1.9 | 121 ± 13 | 119 ± 12 | −1.5 | 119 ± 18 | 118 ± 14 | −0.2 |
| Diastolic BP | 76 ± 10 | 74 ± 9 | −2.5 | 74 ± 9 | 73 ± 9 | −1.7 | 75 ± 9 | 72 ± 9 | −3.5 |

WU = WakeUp ® composition 3.

The invention claimed is:

1. A method for ameliorating, inhibiting or reducing post lunch dip in a subject, the method comprising:
   administering to said subject a composition consisting essentially of an effective amount of an isolate of guarana plant, an effective amount of an isolate of *ginkgo biloba* plant, fruit sugars, and optionally one or more additional ingredient selected from the group consisting of elderberry extract, sugar, sucralose, citric acid, potassium sorbate, and lemon grass,
   wherein the composition comprises between about 30 mg guarana isolate to about 70 mg guarana isolate and between about 30 mg *ginkgo biloba* isolate to about 70 mg *ginkgo biloba* isolate,
   wherein the composition does not affect the subject's heart activity, and
   wherein the effective amount of the isolate of guarana plant and/or the effective amount of the isolate of *ginkgo biloba* plant is effective in ameliorating, inhibiting or reducing post lunch dip.

2. The method of claim 1, further comprising determining the subject's heart activity by one or more parameters selected from the group consisting of heart rate and blood pressure.

3. The method of claim 1, further comprising determining heart activity within a time window of up to 24 hours post administration of said composition.

4. The method of claim 1, wherein administering comprises daily administration of the composition for a period of at least 7 days.

5. The method of claim 4, wherein said daily administration comprises administering the composition once or twice a day.

6. The method of claim 1, wherein administering comprises administration of said composition for at least thirty days.

7. The method of claim 1, wherein administering comprises administration of said composition during or before post lunch dip is developed.

8. The method of claim 1, wherein administering comprises administration of said composition before noon or within a time window of up to an hour before post lunch dip is developed in a subject in need thereof.

9. The method of claim 1, wherein fruit sugars are present in an amount between about 4 ml to about 15 ml.

10. The method of claim 1, wherein the isolate of guarana plant comprises between about 6 mg guaranine to about 20 mg guaranine, the isolate of *ginkgo biloba* plant comprises between 6 mg flavonoid glycosides to about 20 mg flavonoid glycosides and the fruit sugars are present in an amount between about 6 ml to about 10 ml.

11. The method of claim 1, wherein in 100 ml of said composition, the elderberry is present in an amount between about 40 mg to about 60 mg.

12. The method of claim 1, wherein the composition is in a form suitable for oral consumption.

13. A method for affecting post lunch dip in a subject comprising administering to the subject a daily dose of composition consisting essentially of an isolate of guarana plant, an isolate of *ginkgo biloba* plant or functional analogue thereof, fruit sugars and optionally one or more additional ingredient selected from the group consisting of elderberry extract, sugar, sucralose, citric acid, potassium sorbate, and lemon grass, for a period of at least 7 days, wherein said administration provides an effect on said subject selected from the group consisting of ameliorating, inhibiting and reducing post lunch dip.

14. The method of claim 13, further comprising determining the subject's heart activity by one or more parameters selected from the group consisting of heart rate, blood pressure and body temperature.

15. A method for ameliorating, inhibiting or reducing post lunch dip in a subject, comprising administering to said subject a composition comprising an isolate of guarana plant, an isolate of *ginkgo biloba* plant, fruit sugars, elderberry extract, sugar, sucralose, citric acid, potassium sorbate, and lemon grass,
   wherein the effective amount of an isolate of guarana plant and/or the effective amount of an isolate of *ginkgo biloba* plant is effective in ameliorating, inhibiting or reducing post lunch dip.

16. A method for ameliorating, inhibiting or reducing post lunch dip in a subject, the method comprising administering to said subject a composition comprising an isolate of guarana plant, an isolate of *ginkgo biloba* plant, fruit sugars, elderberry extract, sugar, sucralose, citric acid, potassium sorbate, and lemon grass,
   wherein the composition comprises, between about 30 mg guarana isolate to about 70 mg guarana isolate and between about 30 mg *ginkgo biloba* isolate to about 70 mg *ginkgo biloba* isolate, wherein the composition does not affect the subject's heart activity, and wherein the effective amount of an isolate of guarana plant and/or the effective amount of an isolate of *ginkgo biloba* plant is effective in ameliorating, inhibiting or reducing post lunch dip.

* * * * *